United States Patent
Wu et al.

(10) Patent No.: US 11,633,158 B2
(45) Date of Patent: Apr. 25, 2023

(54) FILTERING SYSTEM AND FILTERING METHOD

(71) Applicant: Quanta Computer Inc., Taoyuan (TW)

(72) Inventors: Pei-Sheng Wu, Taoyuan (TW);
Peng-Zhe Tsai, Taoyuan (TW);
Yung-Ming Chung, Taoyuan (TW)

(73) Assignee: QUANTA COMPUTER INC., Taoyuan (TW)

( * ) Notice: Subject to any disclaimer, the term of this patent is extended or adjusted under 35 U.S.C. 154(b) by 291 days.

(21) Appl. No.: 17/000,722

(22) Filed: Aug. 24, 2020

(65) Prior Publication Data
US 2021/0321949 A1     Oct. 21, 2021

(30) Foreign Application Priority Data
Apr. 21, 2020  (TW) ................... 109113262

(51) Int. Cl.
| A61B 5/00 | (2006.01) |
| A61B 7/04 | (2006.01) |
| A61B 5/08 | (2006.01) |
| A61B 7/00 | (2006.01) |

(52) U.S. Cl.
CPC ............. *A61B 5/725* (2013.01); *A61B 5/08* (2013.01); *A61B 5/7203* (2013.01); *A61B 7/003* (2013.01); *A61B 7/04* (2013.01)

(58) Field of Classification Search
CPC ......... A61B 5/725; A61B 5/08; A61B 5/7203; A61B 7/003
See application file for complete search history.

(56) References Cited

U.S. PATENT DOCUMENTS

| 11,083,414 B2* | 8/2021 | Lin ...................... A61B 5/0816 |
| 2006/0198533 A1* | 9/2006 | Wang ...................... A61B 7/00 381/94.1 |
| 2009/0254139 A1* | 10/2009 | Bjorling .................. A61B 7/04 607/17 |
| 2014/0148711 A1* | 5/2014 | Yang .................. A61B 5/0205 600/484 |
| 2022/0005491 A1* | 1/2022 | Mo .......................... A61B 7/02 |

FOREIGN PATENT DOCUMENTS

| CN | 1488319 A | 4/2004 |
| CN | 109545239 A | 3/2019 |

* cited by examiner

*Primary Examiner* — Andrew L Sniezek
(74) *Attorney, Agent, or Firm* — McClure, Qualey & Rodack, LLP

(57) ABSTRACT

A filtering method includes the following steps: receiving an sound signal; decomposing the sound signal into a primary lung sound signal and a reference heart sound signal; adjusting the reference heart sound signal according to a weighted value to generate an adjusted heart sound signal; and subtracting the adjusted heart sound signal from the primary lung sound signal to generate a filtered lung sound signal.

7 Claims, 8 Drawing Sheets

| analysis target | P-value |
|---|---|
| aortic stenosis and crackling sound | 0.0005 |
| wheezing and normal heart sound | 0.0092 |
| snoring sound and normal heart sound | 0.0003 |
| mitral valve insufficiency and normal breathing | 0.0013 |

RS1

800(LHR)

LHR analysis result

| disease position | period | input LHR(dB) | output LHR(dB) | time(sec.) |
|---|---|---|---|---|
| aortic stenosis and tricuspid crackling sound | 1 | 5.4216 | 12.4783 | 0.4~1.2 |
| | 2 | 11.975 | 38.9843 | 4.95~5.7 |
| | 3 | 3.8147 | 14.7006 | 10.9~11.7 |
| | 4 | 3.5856 | 12.5648 | 13.95~14.7 |
| aortic stenosis and aortic valve crackling sound | 1 | 17.9624 | 22.1053 | 2.5~3.6 |
| | 2 | 15.6956 | 19.8516 | 7.5~8.55 |
| | 3 | 9.3503 | 17.1292 | 10.5~11.45 |
| | 4 | 18.0423 | 42.3132 | 19.4~20.5 |
| arterial stenosis and left upper lung crackling sound | 1 | 11.1288 | 26.6803 | 2.1~2.9 |
| | 2 | 10.6098 | 35.6067 | 7.3~8 |
| | 3 | 6.6613 | 43.1605 | 13.65~14.35 |
| | 4 | 10.4912 | 18.3153 | 16.6~17.35 |

FILTERING SYSTEM AND FILTERING METHOD

CROSS REFERENCE TO RELATED APPLICATIONS

This application claims priority of Taiwan Patent Application No. 109113262, filed on Apr. 21, 2020, the entirety of which is incorporated by reference herein.

BACKGROUND OF THE INVENTION

Field of the Invention

The present disclosure relates to a filtering system and a filtering method and, in particular, to a filtering system and a filtering method for processing audio.

Description of the Related Art

The traditional stethoscope mainly relies on the doctor's hearing to distinguish the difference between heart sounds and lung sounds. Nowadays, the filtering methods adopted by electronic stethoscopes such as eKuore and 3M have the disadvantage of filtering out most lung sounds while filtering out heart sounds.

Therefore, how to separate the heart sound noise to obtain the lung sound signal and avoid situations where the heart lung sound is filtered out at the same time has become one of the problems to be solved in the art.

BRIEF SUMMARY OF THE INVENTION

In accordance with one feature of the present invention, the present disclosure provides a filtering system. The filtering system includes an input and output interface and an adaptive filtering device. The input and output interface is configured to receive a sound signal. The adaptive filtering device is configured to decompose the sound signal into a primary lung sound signal and a reference heart sound signal, adjust the reference heart sound signal according to a weighted value to generate an adjusted heart sound signal, and subtract the adjusted heart sound signal from the primary lung sound signal to generate a filtered lung sound signal.

In accordance with one feature of the present invention, the present disclosure provides a filtering method. The filtering method comprises the following steps: receiving an sound signal; decomposing the sound signal into a primary lung sound signal and a reference heart sound signal; adjusting the reference heart sound signal according to a weighted value to generate an adjusted heart sound signal; and subtracting the adjusted heart sound signal from the primary lung sound signal to generate a filtered lung sound signal.

Based on the description above, with the filtering system and filtering method of this case, heart sound noise can be separated from the sound signal of the heart and lung sounds to obtain the lung sound signal, and to avoid situations in which the heart and lung sounds are filtered out at the same time. As such, the filtering system and filtering method achieve the effect of retaining high-component lung sounds.

BRIEF DESCRIPTION OF THE DRAWINGS

In order to describe the manner in which the above-recited and other advantages and features of the disclosure can be obtained, a more detailed description of the principles briefly described above will be rendered with reference to specific examples illustrated in the appended drawings. Understanding that these drawings depict only example aspects of the disclosure and are not therefore to be considered to be limiting of its scope, the principles herein are described and explained with additional specificity and detail through the use of the accompanying drawings, in which:

FIG. 8 is a schematic diagram illustrating a LHR indicator analysis result according to an embodiment of the present invention.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

The present invention will be described with respect to particular embodiments and with reference to certain drawings, but the invention is not limited thereto and is only limited by the claims. It will be further understood that the terms "comprises," "comprising," "includes" and/or "including," when used herein, specify the presence of stated features, integers, steps, operations, elements, and/or components, but do not preclude the presence or addition of one or more other features, integers, steps, operations, elements, components, and/or groups thereof.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having the same name (but for use of the ordinal term) to distinguish the claim elements.

Figure 1:
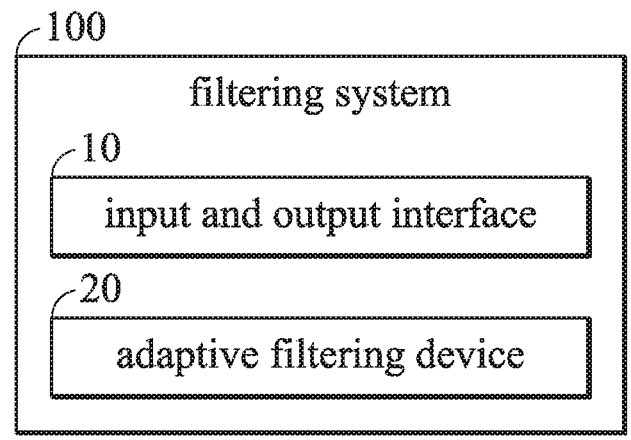
FIG. 1 is a block diagram of a filtering system in accordance with one embodiment of the present disclosure.
Figure 2:
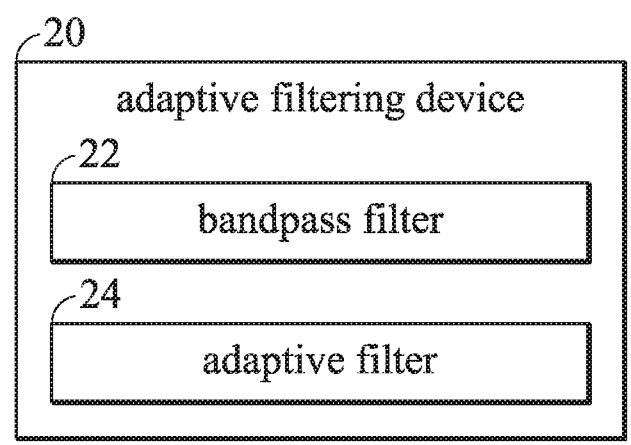
FIG. 2 is a block diagram of an adaptive filtering device in accordance with one embodiment of the present disclosure.
Figure 3:
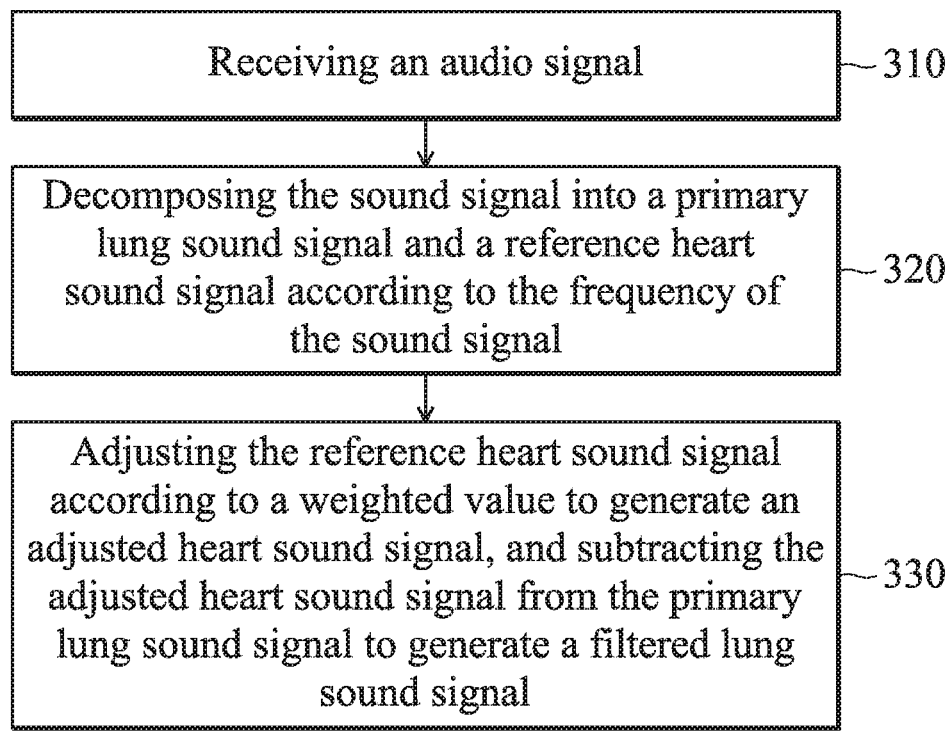
FIG. 3 is a filtering method in accordance with one embodiment of the present disclosure.

FIGS. 1-3 and 3, FIG. 1 is a block diagram of a filtering system 100 in accordance with one embodiment of the present disclosure. FIG. 2 is a block diagram of an adaptive filtering device 20 in accordance with one embodiment of the present disclosure. FIG. 3 is a filtering method 300 in accordance with one embodiment of the present disclosure.

As shown in FIG. 1, the filtering system 100 includes an input and output interface 10 and an adaptive filtering device 20. In one embodiment, the input and output interface 10 may be a Bluetooth transmission device, a wireless or wired network device.

As shown in FIG. 2, the adaptive filtering device 20 includes a bandpass filter 22 and an adaptive filter 24.

In one embodiment, the bandpass filter 22 is a device that allows waves of a specific frequency band to pass while shielding other frequency bands. For example, a resistor, an inductor, and/or a capacitor circuit can be used to implement a bandpass filter 22.

In one embodiment, the order of the bandpass filter is 2nd order or 4th order.

In one embodiment, the adaptive filter 24 is a digital filter that can automatically adjust the performance according to the input signal and perform digital signal processing. For example, the corrected signal is generated based on the input signal and the error signal. For some applications, since some parameters required for operation are not known in advance, such as the characteristics of some noise signals, it is necessary to use adaptive coefficients for processing. In this situation, the adaptive filter 24 may adjust the filter coefficients and frequency response via a feedback mechanism. In one embodiment, the adaptive filter 24 may be implemented by Least Mean Square Filter (LMS) and Recursive Least Square (RLS) method.

In step 310, an input and output interface 10 receives an sound signal.

Figure 4:
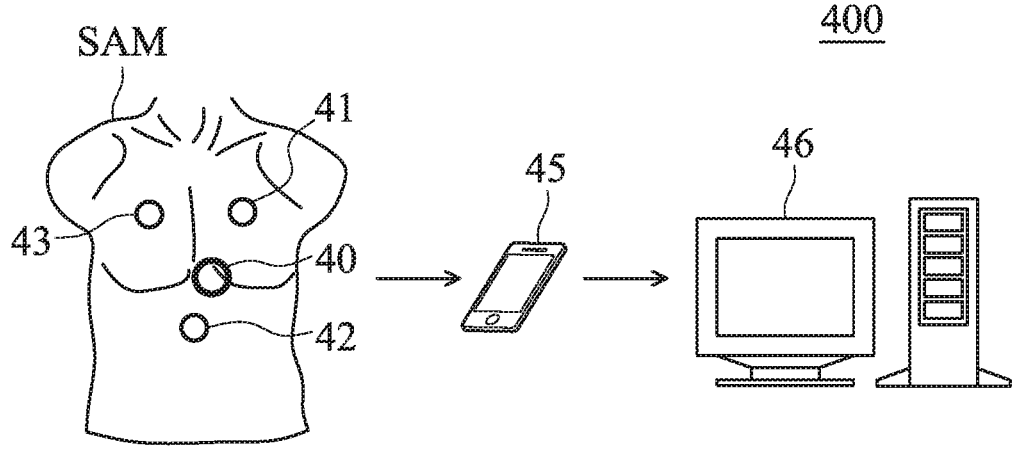
FIG. 4 is a schematic diagram of a filtering system in accordance with one embodiment of the present disclosure.

Please refer to FIG. 4, FIG. 4 is a schematic diagram of a filtering system 400 in accordance with one embodiment of the present disclosure. The electronic device 45 in FIG. 4 may be a mobile phone, a tablet, a smart watch, or other devices with communication, calculation, and display functions. For convenience of description, the following uses a mobile phone as an example for description.

The electronic device 46 in FIG. 4 can include the filter system 100 in FIG. 1. In one embodiment, the electronic device 46 can be a computer, a server, or other devices with communication, calculation, and display functions. For convenience of description, the following uses a computer as an example for description.

In one embodiment, the calculation result calculated by the computer 46 can be transmitted back to the mobile phone 45, which is convenient for the user to operate on the mobile phone 45. On the other hand, the mobile phone 45 can also obtain the signal from the simulator SAM in real time, and then transmit the signal to the computer 46. In another embodiment, the mobile phone 45 can also be equipped with the filtering system 100 of FIG. 1 and can generate the calculation result by itself without passing through the computer 46.

The simulator SAM in FIG. 4 is a human body model that can simulate heart sounds and lung sounds that can be heard in various parts of the human body in different physical conditions. In one embodiment, the simulator SAM is a closed torso model. When the stethoscope 40 is attached to the simulator SAM, the sounds from the upper left lung position 41, the tricuspid valve position 42 and the aortic valve position 43 can be heard at different positions. For example, when the stethoscope 40 is placed near the upper left lung position 41 of the simulator SAM, the sound from the left upper lung position 41 can be heard loudly, and those from the tricuspid valve position 42 and the aortic valve position 43 can be heard relatively quiet.

Figure 6:
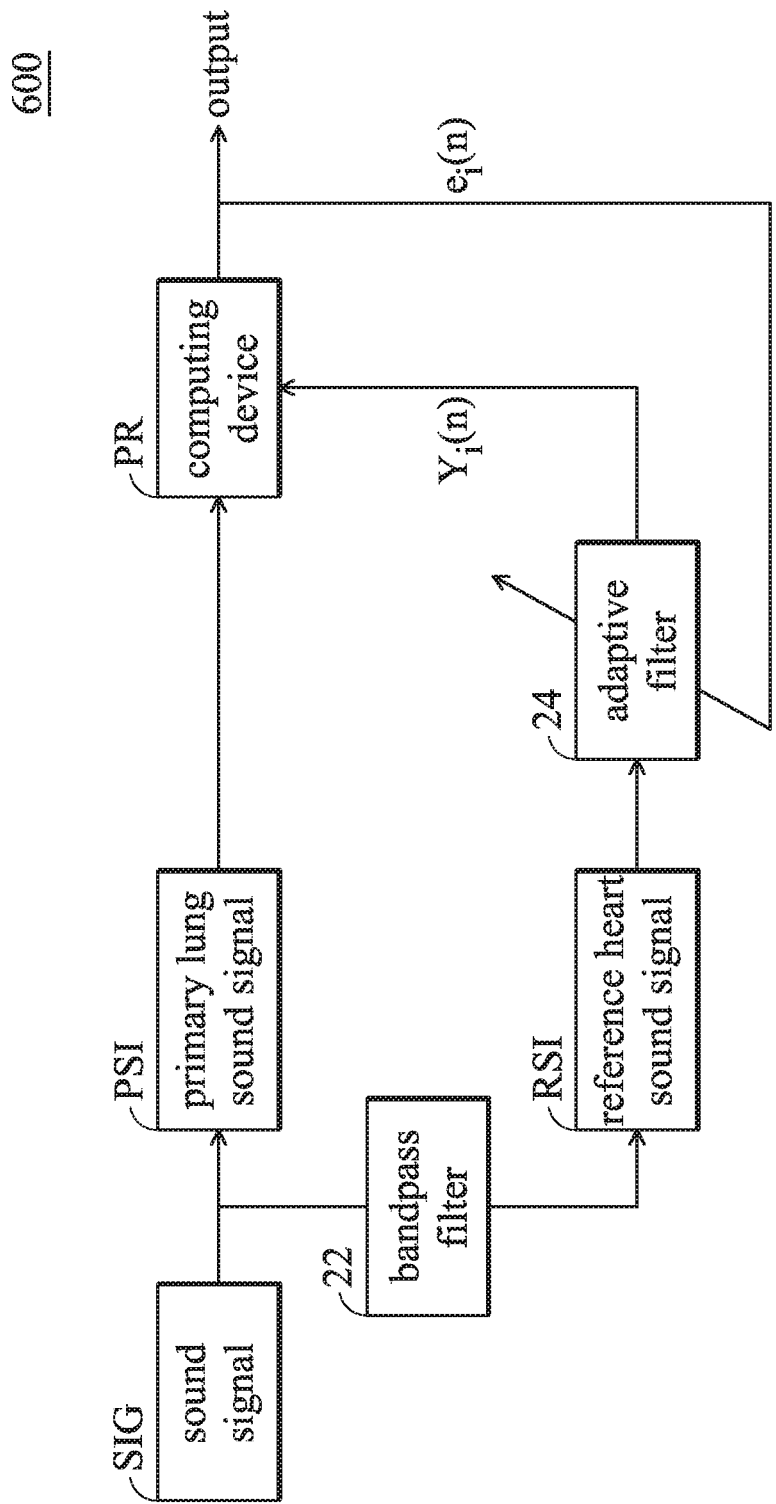
FIG. 6 is a schematic diagram of an adaptive filtering method in accordance with one embodiment of the present disclosure.

In one embodiment, the stethoscope 40 includes an analog-to digital converter. The stethoscope 40 transforms the received sound into digital audio and transmits or outputs the digital audio to the mobile phone 45. The mobile phone 45 then transmits digital audio (i.e., the sound signal SIG, as shown in FIG. 6) to the computer 46. In one embodiment, the stethoscope 40 can also directly send the digital audio (i.e., sound signal SIG) to the computer 46. In one embodiment, the digital audio is, for example, a lossless audio file, such as a WAV format audio file.

Figure 5:
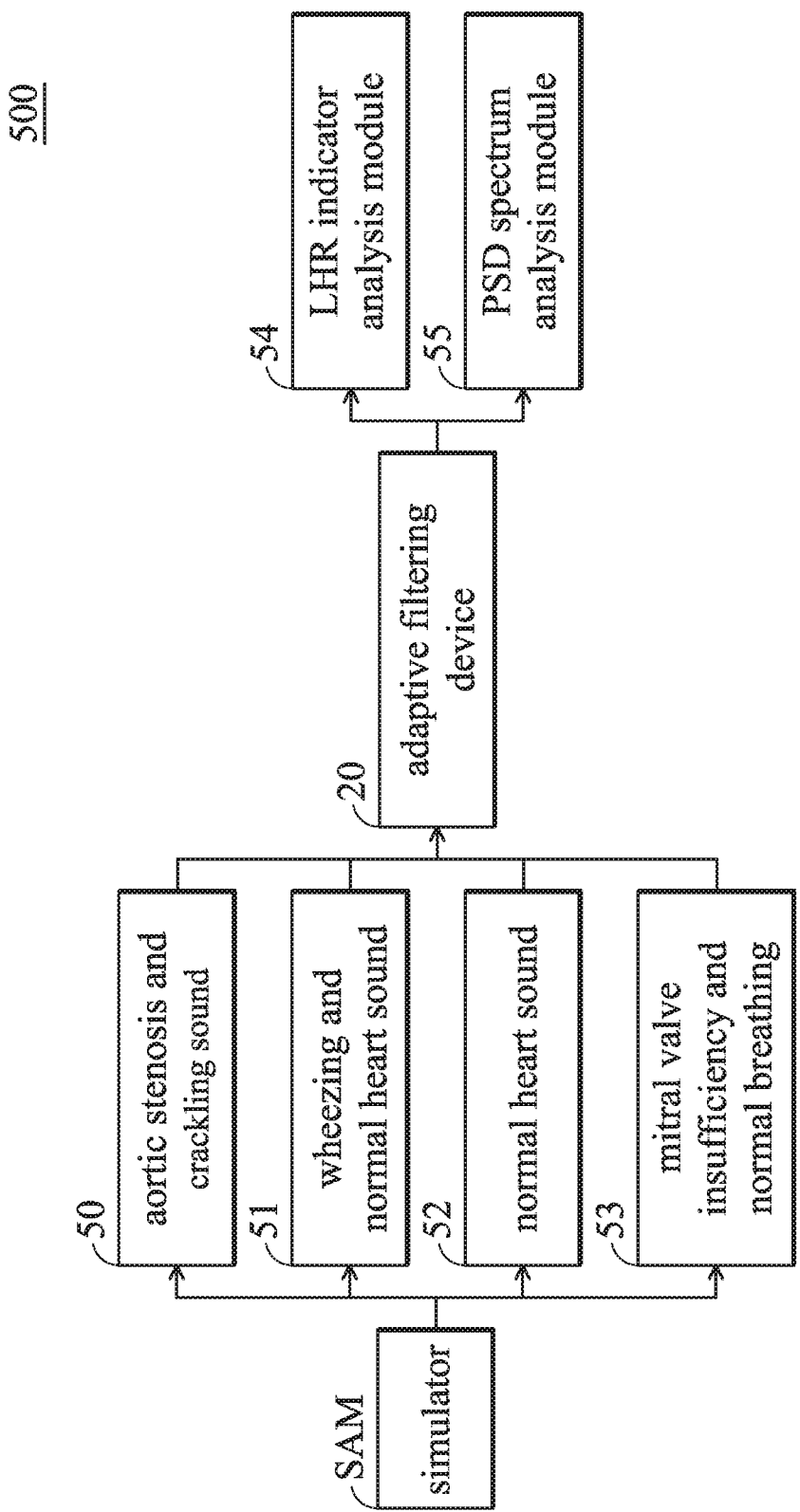
FIG. 5 is a schematic diagram of a testing architecture of a filtering method in accordance with one embodiment of the present disclosure.

Please refer to FIG. 5, FIG. 5 is a schematic diagram of a testing architecture 500 of a filtering method in accordance with one embodiment of the present disclosure. In FIG. 5, the simulator SAM is set to keep reserving the heart sounds and lung sounds, so that the simulator SAM simulates four symptoms, namely aortic stenosis and crackling sound 50, wheezing and normal heart sound 51, snoring and normal heart sound 52 and mitral valve insufficiency and normal breathing 53. For each symptom, three positions are measured, namely the left upper lung position 41, the tricuspid valve position 42 and the aortic valve position 43. After measuring the signal (that is, the sound signal SIG) and transmitting it to the computer 46 through the stethoscope 40, the computer 46 processes the adaptive filtering device 20 of the filtering system 100, and then the computer 46 triggers the lung sounds to heart sounds ratio (LHR) indicator analysis module 54 and power spectral density (PSD) spectrum analysis module 55.

In step 320, the adaptive filtering device 20 decomposes the sound signal SIG into a primary lung sound signal PSI and a reference heart sound signal RSI according to the frequency of the sound signal SIG.

Please refer to FIG. 6, FIG. 6 is a schematic diagram of an adaptive filtering method 600 in accordance with one embodiment of the present disclosure. After receiving the sound signal SIG, the adaptive filtering device 20 transmits the sound signal SIG to the bandpass filter 22. The bandpass filter 22 filters the sound signal SIG into a filtered signal of 20 to 300 hertz (Hz) as an output. This output is regarded as the reference heart sound signal RSI.

In step 330, the adaptive filter device 20 adjusts the reference heart sound signal RSI according to a weighted value to generate an adjusted heart sound signal $Y_i(n)$, and subtracts the adjusted heart sound signal $Y_i(n)$ from the primary lung sound signal PSI to generate a filtered lung sound signal $e_i(n)$.

In one embodiment, the symbol i in the adjusted heart sound signal $Y_i(n)$ and the filtered lung sound signal $e_i(n)$ represents the number of iterations (for example, for the first calculation i equals to 1, and for the second calculation i equals to 2). The symbol n represents the current signal (for example, the next signal is expressed as n+1). After filtering, the filtered lung sound signal $e_i(n)$ is the output signal, which is fed back to the adaptive filter 24 for adjusting the parameters in the adaptive filter 24. The number of feedback iterations (that is, the symbol i, for example, i is a value between 0-100) can be defined in advance, or an accuracy threshold can be defined. When the adaptive filter 24 determines that the accuracy of the lung sound signal $e_i(n)$ after filtering is greater than the accuracy threshold, it means that the weighted value tends to be stable. In other words, a more pure lung sound has been extracted (for example, the lung sound in the filtered lung sound signal $e_i(n)$ is higher than 99%).

In one embodiment, the adaptive filter 24 is used to generate a weighted value to subtract the adjusted heart sound signal $Y_i(n)$ from the primary lung sound signal PSI through a computing device (such as a processor or software operation) PR to output a filtered lung sound signal $e_i(n)$. The filtered lung sound signal $e_i(n)$ is fed back to the adaptive filter 24, and the adaptive filter 24 generates an updated weighted value according to the weighted value and the filtered lung sound signal $e_i(n)$. This updated weighted value can adjust the next signal to filter out more heart sounds. In one embodiment, the weighted value is between −1 and 1.

In one embodiment, if the weighted value is represented as $W(n)$, the reference heart sound signal RSI is represented as $h_i(n)$, and the symbol n represents the current signal, then after performing the inner product operation on the weighted value $W(n)$ and the reference heart sound signal $h_i(n)$, the adjusted heart sound signal $Y_i(n)$ can be obtained.

In one embodiment, the primary lung sound signal PSI is represented as $X_i(n)$, the symbol i represents the number of iterations, the symbol n represents the current signal, and the adjusted heart sound signal $Y_i(n)$ is subtracted from the primary lung sound signal $X_i(n)$ to generate the filtered lung sound signal $e_i(n)$.

In one embodiment, the filtered lung sound signal $e_i(n)$ is fed back to the adaptive filter 24 for adjusting the next signal, then the weight of the next signal n+1 can be expressed as $W(n+1)$. The adaptive filter 24 adds the weighted value $W(n)$ to the inner product of the step size and the reference heart sound signal $h_i(n)$ and the filtered lung sound signal $e_i(n)$ (the mathematical formula can be presented as $W(n+1)=W(n)+\text{step size} \cdot h_i(n) \cdot e_i(n)$), and then the weight $W(n+1)$ of the next signal n+1 can be obtained. In this way, the weight $W(n+1)$ can be reused to generate a more accurate filtered lung sound signal.

For example, if the first filtered lung sound signal $e1(n)$ contains 10% lung sound (for example, the filtered lung sound signal $e1(n)$ divided by the primary lung sound signal $X1(n)$ is 10%. However, the algorithm or evaluation method here is not limited thereto). After 10 iterations (i=10), the tenth filtered lung sound signal $e10(n)$ contains 99% of lung sounds (the values here are for illustration only, and a lung sound threshold can also be preset. When the proportion of lung sound is higher than the lung sound threshold, it means that the adaptive filter 24 (weighted value) tends to be stable). In this way, the accuracy of the filtered lung sound signal $e_i(n)$ generated by the adaptive filter 24 can be improved.

In one embodiment, the step size of the adaptive filter 24 is less than 0.03

In one embodiment, the step size of the adaptive filter 24 is 0.006.

In one embodiment, the window size of the adaptive filter 24 is less than 256 audio points. The window width can reduce the discontinuity of the start and end signals in the audio. Since the concept of the window width of the adaptive filter 24 is a known technology, it will not be discussed here.

This step can filter out the heart sound part from the sound signal SIG, and extract the pure lung sound, which can help the medical personnel to judge the lung sound.

Figure 7:
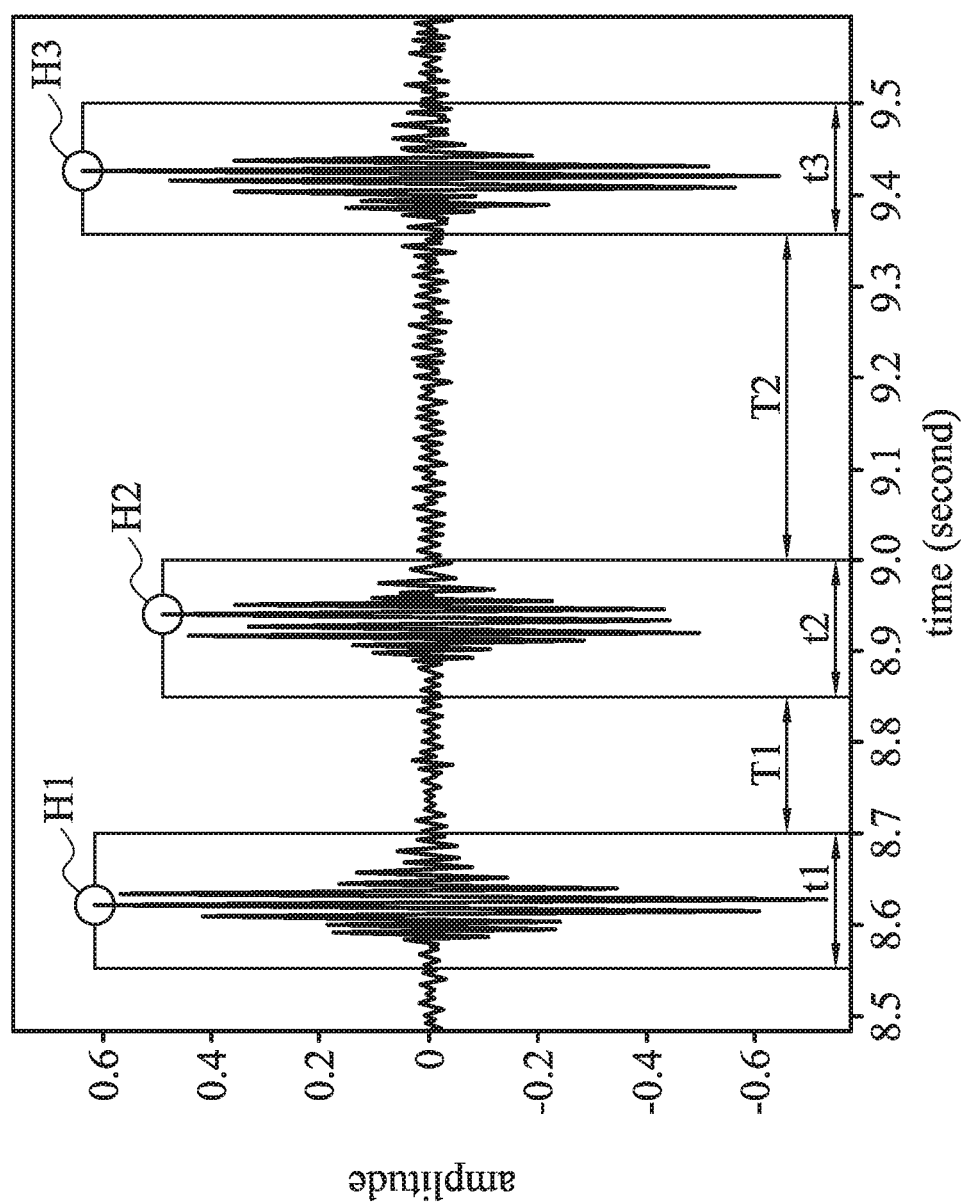
FIG. 7 is a schematic diagram illustrating a LHR indicator analysis method according to an embodiment of the present invention.

Please refer to FIG. 7, FIG. 7 is a schematic diagram illustrating a LHR indicator analysis method 700 according to an embodiment of the present invention. FIG. 7 is the sound signal diagram of the heart and lung sounds (normalized), the vertical axis is amplitude and the horizontal axis is time (seconds). The method of the LHR indicator analysis method 700 is to capture the highest point H1 of the first heart sound (the highest amplitude point) and the highest point H2 of the second heart sound. Take the highest point H1 of the first heart sound as the center, expanding to the left and right, moving in the smallest unit of 0.05 seconds. If the amplitude is greater than 0.1, the expansion continues until the recognition of the heart sound boundary is completed, and the first heart sound interval t1 can be obtained. The highest point H2 of the second heart sound and the highest point H3 of the third heart sound are processed in the same way as the first heart sound, so the second heart sound interval t2 and the next heart sound interval t3 can also be found. The interval between the occurrence of every two heart sounds (such as T1 and T2) is regarded as the interval of lung sounds. This completes the cardiopulmonary sound determination rule, and this determination rule is input into the LHR indicator analysis module 54.

In one embodiment, the LHR indicator analysis module 54 can be implemented by software or hardware circuits. The LHR indicator analysis module 54 can determine the difference between the filtering method 300 and without adopting the filtering method 300 in terms of timing.

Please refer to FIG. 8, FIG. 8 is a schematic diagram illustrating a LHR indicator analysis result 800 according to an embodiment of the present invention. The analysis targets in FIG. 8 are divided into: four simulated symptoms of the measurement simulator SAM, which are aortic stenosis and crackling sound, wheezing and normal heart sound, snoring sound and normal heart sound, and mitral valve insufficiency and normal breathing. P-value represents the probability that the test statistic shows a certain value that should not be when the original hypothesis is true. Usually P-value less than 0.05 means that the component of the lung sound signal output by adopting the filtering method 300 is high enough. That is, there is a significant difference before and after filtering.

Taking the analysis target RS1 of the aortic stenosis and crackling sound as an example, it can be seen from the LHR analysis result RS1 that each disease measures three positions, that is, the left upper lung position 41, the tricuspid valve position 42, and the aorta valve position 43. Each measurement position is divided into 4 periods, for example, the position of the tricuspid valve of aortic stenosis and crackling sound is divided into 4 periods (0.4 s-1.2 s, 4.95 s-5.7 s, 10.9 s-11.7 s, 13.98 s-14.7 s) for analysis. In this way, it can be seen that the decibel change of the input LHR (representing the original data, without using the filtering method 300) data and the output LHR data (representing using the filtering method 300) at different timings at this location. Overall, it can be seen that the decibel (dB) of the output LHR data using the filtering method 300 is greater than the decibel of the input LHR data. From the LHR analysis results, it can be seen that the filtering method 300 can make the lung sound more clear.

Figure 9:
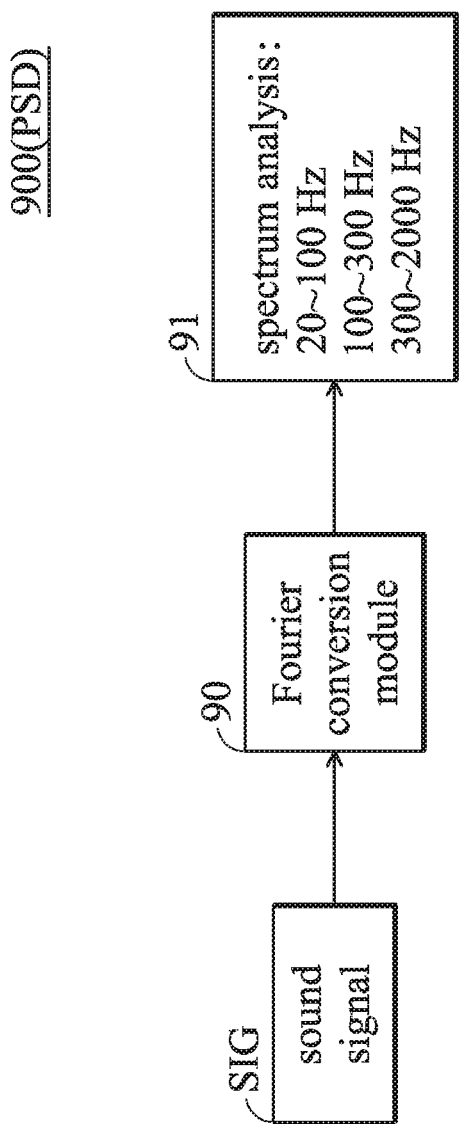
FIG. 9 is a schematic diagram illustrating a PSD spectrum analysis method according to an embodiment of the present invention.

Please refer to FIG. 9, FIG. 9 is a schematic diagram illustrating a PSD spectrum analysis method 900 according to an embodiment of the present invention. The PSD spectrum analysis module 55 can send the sound signal SIG to a Fourier transform (FFT) module 90 for mathematical operation, and the window size can be 8192. After Fourier transform, multiple frequency bands 91 can be analyzed, for example, 20-100 Hz, 100-300 Hz, 300-2000 Hz.

In one embodiment, the Fourier conversion module 90 can be implemented by software or hardware circuits.

In one embodiment, the PSD spectrum analysis module 55 can be implemented by software or hardware circuits. The PSD spectrum analysis module 55 can determine the difference between adopting the filtering method 300 and without adopting the filtering method 300 on the frequency band.

Figure 10:
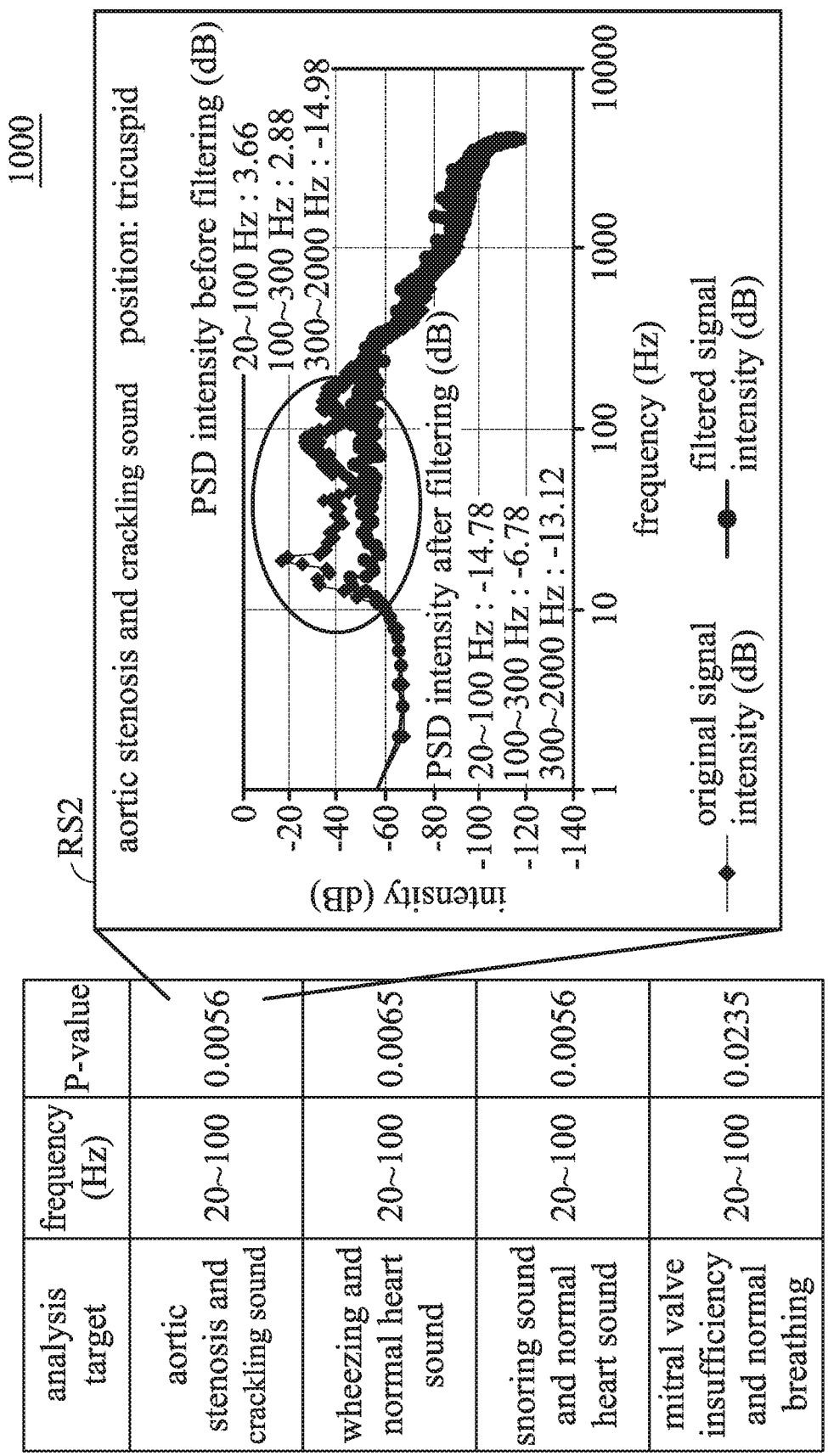
FIG. 10 is a schematic diagram illustrating a PSD spectrum analysis result according to an embodiment of the present invention.

Please refer to FIG. 10, FIG. 10 is a schematic diagram illustrating a PSD spectrum analysis result 1000 according to an embodiment of the present invention. In FIG. 10, the vertical axis is intensity (dB), and the horizontal axis is frequency (Hz). The analysis targets in FIG. 10 are divided into: four simulated symptoms of the measurement simulator SAM, which are aortic stenosis and crackling sound, wheezing and normal heart sound, snoring sound and normal heart sound, and mitral valve insufficiency and normal breathing. P-value represents the probability that the test statistic shows a certain value that should not be when the original hypothesis is true. Usually P-value less than 0.05 means that the component of the lung sound signal output by adopting the filtering method 300 is high enough. That is, there is a significant difference before and after filtering. It can be seen from FIG. 10 that the P-values of the four simulated symptoms of the simulator SAM are all less than 0.05, which represents a significant difference between before and after filtering.

Take the PSD analysis result RS2 of the aortic stenosis and crackling sound at the tricuspid valve as an example. The value in the PSD analysis result RS2 can be the data, which after normalization adjustment. In FIG. 10, the PSD intensity (dB) before filtering is 3.66 at 20-100 Hz, 2.88 at 100-300 Hz, and −14.98 at 300-2000 Hz. On the other hand, the filtered PSD intensity is −14.78 at 20-100 Hz, −6.78 at 100-300 Hz, and −13.12 at 300-2000 Hz. After filtering, some heart sound signals are filtered out. Therefore, the PSD intensity will be lower than the PSD intensity before filtering.

More specifically, in FIG. 10, since the frequency of general heart sounds is about 20-100 Hz, so this frequency is taken as representative. From the PSD spectrum analysis result RS2, it can be seen that after the frequency of heart sounds (20-100 Hz) is filtered, some heart sound signals are filtered out. In addition, from the circled in RS2 of the PSD spectrum analysis result, it can also be seen that the original signal intensity is higher due to the mixing of heart sounds and lung sounds. After the signal processing by the filtering method 300, part of the heart sound is obviously filtered out, so the signal intensity is relatively low, which means that part of the heart sound is filtered out, making the lung sound signal relatively sound clearer (that is, a more pure lung sound signal).

Based on the description above, with the filtering system and filtering method of this case, heart sound noise can be separated from the sound signal of the heart and lung sounds to obtain the lung sound signal, and to avoid having the heart and lung sounds filtered out at the same time. As such, the filtering system and filtering method achieve the effect of retaining high-component lung sounds.

Although the invention has been illustrated and described with respect to one or more implementations, equivalent alterations and modifications will occur or be known to others skilled in the art upon the reading and understanding of this specification and the annexed drawings. In addition, while a particular feature of the invention may have been disclosed with respect to only one of several implementations, such a feature may be combined with one or more other features of the other implementations as may be desired and advantageous for any given or particular application.

What is claimed is:

1. A filtering system, comprising:
    an input and output interface, configured to receive an sound signal; and
    an adaptive filtering device, configured to decompose the sound signal into a primary lung sound signal and a reference heart sound signal, adjust the reference heart sound signal according to a weighted value to generate an adjusted heart sound signal, and subtract the adjusted heart sound signal from the primary lung sound signal to generate a filtered lung sound signal;
    wherein the adaptive filtering device further comprises:
        a bandpass filter, configured to filter the sound signal into a filtered signal of 20-300 hertz (Hz) as the reference heart sound signal; and
        an adaptive filter, configured to generate the weighted value, and subtract the adjusted heart sound signal from the primary lung sound signal to output the filtered lung sound signal;
    wherein a step size of the adaptive filter is less than 0.03.

2. The filtering system of claim 1, wherein the filtered lung sound signal is fed back to the adaptive filter, and the adaptive filter generates an updated weighted value according to the weighted value and the filtered lung sound signal.

3. The filtering system of claim 2, wherein the step size of the adaptive filter is 0.006.

4. The filtering system of claim 2, wherein a window size of the adaptive filter is less than 256 audio points.

5. The filtering system of claim 1, wherein order of the bandpass filter is 2nd order or 4th order.

6. A filtering method, comprising:
    receiving an sound signal;
    decomposing the sound signal into a primary lung sound signal and a reference heart sound signal;
    adjusting the reference heart sound signal according to a weighted value to generate an adjusted heart sound signal, wherein the weighted value is generated by an adaptive filter, and a step size of the adaptive filter is less than 0.03;
    subtracting the adjusted heart sound signal from the primary lung sound signal to generate a filtered lung sound signal; and
    filtering the sound signal into a filtered signal of 20-300 hertz (Hz) as the reference heart sound signal.

7. The filtering method of claim 6, further comprising:
    generating the weighted value;
    subtracting the adjusted heart sound signal from the primary lung sound signal to output the filtered lung sound signal;
    feeding back the filtered lung sound signal to an adaptive filter; and
    generating an updated weighted value according to the weighted value and the filtered lung sound signal.

* * * * *